United States Patent [19]

Gebauer

[11] Patent Number: 5,041,646

[45] Date of Patent: Aug. 20, 1991

[54] PROCESS FOR PRODUCING 2-METHYL-2-BUTENOIC ACID

[75] Inventor: Helmut Gebauer, Munich, Fed. Rep. of Germany

[73] Assignee: Consortium fur elektrochemische Industrie GmbH, Munich, Fed. Rep. of Germany

[21] Appl. No.: 899,204

[22] Filed: Aug. 22, 1986

[30] Foreign Application Priority Data

Oct. 8, 1985 [DE] Fed. Rep. of Germany ....... 3535889

[51] Int. Cl.$^5$ ..................... C07C 51/08; C07C 57/03
[52] U.S. Cl. ..................................... 562/598; 203/69; 562/600
[58] Field of Search ........................................ 562/598

[56] References Cited

U.S. PATENT DOCUMENTS

| | | | |
|---|---|---|---|
| 3,320,305 | 5/1967 | Wiese | 562/598 |
| 3,381,034 | 4/1968 | Greene et al. | 562/598 |
| 3,515,750 | 6/1970 | Schroder et al. | 562/598 |
| 3,876,691 | 4/1975 | Lincoln | 562/598 |
| 4,613,680 | 9/1986 | Naruto et al. | 562/598 |

OTHER PUBLICATIONS

Buckles et al., Chem. Reviews, 55, 659–677 (1955).
Demarcay, Chem. Ber., 9, 1933 (1876).

*Primary Examiner*—Vivian Garner
*Attorney, Agent, or Firm*—Collard, Roe & Galgano

[57] ABSTRACT

A process for producing cis-2-methyl-2-butenoic acid, which process is preferably based on technical 2-methyl-2-butene nitrile and leads to pure products preferably without costly rectification. The technical nitrile is hydrolyzed by concentrated sulfuric acid at temperatures of up to 130° C. and, following dilution of the sulfuric acid to about 50%, at temperatures of up to 130° C. It is treated by distilling and fractional crystallization.

11 Claims, No Drawings

PROCESS FOR PRODUCING 2-METHYL-2-BUTENOIC ACID

This invention relates to a novel process for producing Z-2-methyl-2-butenoic acid (2-methyl-isocrotonic acid; angelic acid; angelica acid; 2-methyl-cis-crotonic acid). The acid exists in nature, for example, as an ingredient of angelica root oil, among other sources. Some of the esters of the acid are key ingredients of the Roman camomile oil, which is highly desired and, as such, are important scent or fragrance carriers. The acid and its esters, thus, are useful as fragrances and flavoring agents.

However, in spite of the fact that the perfume-manufacturing industry and processors using flavoring substances are highly interested in such substances, no economical process for producing such compounds is presently known. European Patent Application No. 0112394 does propose a synthesis of angelica acid and its esters by thermal rearrangement of the isomeric tigline compounds by means of organic sulfinic acids as the catalyst. Such a process, however, requires valuable fragrances as starting materials (tiglic acid or tiglates) and, furthermore, requires high expenditures in terms of equipment and energy. Because of the Z-configuration or cis-configuration, Z-2-methyl-2-butenoic acid and its esters are thermally less stable than the corresponding trans- configuration (tiglic acid; tiglates). Therefore, the isomerization equilibrium, at most, contains 10% cis-configuration in the mixture. Owing to the fact that angelica acid and its esters melt and boil at a few degrees below the corresponding tiglic acid or tiglates, the isomers may be separated by means of costly rectification. This procedure, in the above-identified European patent application, is referred to as "isomerization distillation."

It is, therefore, an object of the present invention to provide a simpler and less costly way of producing cis-2-methyl-2-butenoic acid from low-cost or less expensive starting materials with the highest yields possible, while simultaneously yielding the lowest possible content of trans-2-methyl-2-butenoic acid in the crude product.

Other objects and features of the present invention will become apparent from the following description of the invention.

The foregoing and related objects are achieved by the present invention which concerns a process for producing cis-2-methyl-2-butenoic acid by sulfuric hydrolysis of 2-methyl-2-butene nitrile, which may contain contaminants, at an elevated temperature followed by crystallization. The process is characterized in that the nitrile is added by dosing, while stirring, to 60 to 100, preferably 75 to 85, and most particularly, 75 to 80% by weight sulfuric acid at temperatures of up to 130° C., preferably up to 80° C., until a molar ratio of nitrile to sulfuric acid of 1 : 3 to 1 : 1 has been reached. The foregoing mixture is subsequently maintained at said temperature until the reaction of the nitrile groups has been completed. The mixture is subsequently diluted to a sulfuric acid content of 40 to 60% by weight, preferably, 45 to 55% by weight, while continuing to stir the mixture and, optionally, under pressure, at temperatures of up to 130° C., preferably up to 100° C., until the reaction to acid is completed. The organic phase is then separated from the aqueous phase, washed and subsequently subjected to distilling at temperatures of up to 199° C., preferably, the organic phase is subjected to vacuum distillation at temperatures of up to 120° C. Following distillation, the distillate is cooled and the crystallized cis-2-methyl-2-butenoic acid is filtered off.

The 2-methyl-2-butene nitrile, which is collected as an industrial by-product in the production of adiponitrile and which, generally, may still contain up to about 40% by weight contaminants, is available on the market, for example, as solvent, or in some cases even incinerated for lack of other possible applications. Even such industrial or technical nitrile may be used and reacted in accordance with the invention. It is preferred as the starting material because no prior purification is required if it is used and reacted according to the invention.

Based on the specification sheet of a company (Rhôue-Poulenc Chimie de Base S.A. F-g2402 Courbevoie Cedex, France) selling such nitrile, the nitrile consists of 60 to 70% by weight of 2-methyl-2-butene nitrile and, generally, up to 6 to 25% by weight of 2-methyl-3-butene nitrile, 0.5 to 9% by weight of cyclohexane, 3 to 7% by weight of vinyl cyclohexene, 0.1 to 4% by weight of cycloactodiene, 0 to 2% by weight of butadiene, and, up to 30 ppm hydrogen cyanide (such components adding up to a total of 100% by weight). Such substances containing contaminants are normally referred to as "technical" substances. Thus, the preferred starting material used in the process of the invention is generally referred to in the present application as technical 2-methyl-2-butene nitrile, or technical nitrile.

If the process is particularly based on such technical nitrile, the process first supplies mixtures containing cis- and trans-2-methyl-2-butenoic acid. Under particularly mild conditions, i.e., according to the preferred way of carrying out the process, the cis- selectivity is very high even when using such technical nitrile, and the isomer ratio comes to, at least, and preferably above 60 : 40, for example, above 65 : 35.

The selectivity of the inventive process is particularly surprising especially when using technical nitrile since it is known from numerous literature sources that the cis-2-methyl-2-butenoic acid and its derivatives readily rearrange themselves to the trans- form, for example in the basic and acid pH ranges (for example in sulfuric acid) and at elevated temperatures (cf, for example, Buckles, Mock and Locatell, *Chem. Reviews*, (1955), 55, pp 659–677).

By the process of the invention, it is possible to produce cis-2-methyl-2-butenoic acid with a purity, preferably, in excess of 95%, especially, in excess of 98%, without high expenditures in terms of equipment and energy requirements, even from technical nitrile, according to the preferred procedure and, in particular, without cumbersome fractionated distillation. Prior to fractionating by crystallization, the distillate, which in the conventional manner is separated from the preceding and succeeding stages, primarily or predominantly consists of cis-and trans-2-methyl-2-butenoic acids, with the trans- acid being unavoidably formed from the 2-methyl-3-butene nitrile. Often, the ratio of cis- to trans-acid is in the range from 75 : 25 to 81 : 19.

If the requirements with respect to selectivity are not sufficiently high, the reaction of the 2-methyl-2-butene nitrile may be carried out with concentrated sulfuric acid, i.e., with a concentration exceeding 85%, in which case, however, partial rearrangement of the cis-2-methyl-2-butenoic acid to trans- acid will occur. The same applies if the temperatures are maintained above the preferred range. On the other hand, if the nitrile is reacted at temperatures below, for example, 70° C., i.e., at temperatures in the range of 20° and 70° C., the reaction times are prolonged or even highly prolonged, which would detract from the economy of the inventive process. Therefore, temperature ranges of 70–80° C. and 70–100° C. are maintained in the two respective stages (b) and (c) of the reaction. While the nitrile is added to the sulfuric acid by dosing, the temperature is, preferably, maintained at a lower level, for example, at below 60° C., and particularly, at e.g., 30° to 55° C.

Preferably, polymerization inhibitors are added to the reaction mixture, for example, a mixture of hydroquinone and zinc sulfate. It was found that it is particularly advantageous if such inhibitors are added in amounts of 0.1 to 1 mole-% based on the amount of nitrile used. Because of its capability of responding to polymerization reactions, the cis-2-methyl-2-butenoic acid may be used also as (co-)monomer in radical polymerizations.

The following example serves for explaining the invention in greater detail (the percentages are based on weight). It should, however, be noted that such example is given by way of illustration and not of limitation.

A crude (technical) nitrile of the following composition (determined by gas-chromatography) was used:

| COMPONENT | % by wt. |
|---|---|
| 2-methyl-2-butene nitrile | 63 |
| 2-methyl-3-butene nitrile | 20 |
| cyclohexane | 5.5 |
| vinyl cyclohexene | 6.6 |
| cyclooctadiene | 1.9 |
| butadiene | 1.1 |
| undefined | 1.9 |

EXAMPLE

A 360-liter enamel-coated vessel with cooling and stirring equipment was loaded with 120 kg 80% sulfuric acid and 100 g each of hydroquinone and zinc sulfate. 81 kg (99 liters) crude nitrile was added within two hours under cooling and stirring, during which period the temperature was maintained at 50° to 55° C.

Following 24 hours of reaction time at 80° C., 80 liters of water were added and stirring was continued for another 32 hours at 100° C. After adding 60 liters of toluene, the phases were separated and the organic phase was distilled.

After removing the low-boiling ingredients, 63.5 kg of product mixture consisting of 80.5% angelica acid and 19.5% tiglic acid was collected in the boiling range of $bp_{12}$ 83–99° C., from which is was possible to separate pure angelica acid by crystallization. Distillation residue: 18 kg.

While only several embodiments and one example of the present invention have been described, it is obvious that many changes and modifications may be made thereunto, without departing from the spirit and scope of the invention.

What is claimed is:

1. A process for producing cis-2-methyl-2-butenoic acid, comprising the steps of
   (a) reacting 2-methyl-2-butene nitrile with 75 to 85% by weight sulfuric acid by adding said nitrile, by means of dosing while stirring the reaction mixture, at a temperature of up to 80° C., until a molar ratio of said nitrile to sulfuric acid of 1:3 to 1:1 has been achieved;
   (b) maintaining said temperature until the reaction of said nitrile has been completed;
   (c) diluting the sulfuric acid content of said reaction mixture to 40 to 60% by weight, while continuing said stirring at a temperature of up to 100° C., until a reaction to said acid is completed; and
   (d) separating and washing said reaction mixture to obtain the organic phase containing said acid;
   (e) distilling said organic phase at a temperature of up to 199° C.;
   (f) cooling the resultant distillate to crystallize said acid; and
   (g) filtering off said acid.

2. The process according to claim 1, wherein said step (e) is carried out by vacuum distillation at a temperature of up to 120° C.

3. The process according to claim 1, wherein a polymerization inhibitor is added to said reaction mixture.

4. The process according to claim 3, wherein said polymerization inhibitor is added to said reaction mixture with a concentration of from 0.1 to 1 mole-%.

5. The process according to claim 3, wherein said polymerization inhibitor is a mixture of hydroquinone and zinc sulfate.

6. The process according to claim 1, wherein 2-methyl-2-butene nitrile is added to 75 to 80% by weight sulfuric acid.

7. The process according to claim 1, wherein the sulfuric acid content of said reaction mixture in said step (c) is diluted to 45 to 55% by weight sulfuric acid.

8. The process according to claim 1, wherein said step (b) is carried out at a temperature of 70° to 80° C.

9. The process according to claim 1, wherein said step (c) is carried out at a temperature of 70° to 100° C.

10. The process of claim 7, wherein said step (a) is carried out at a temperature of below 60° C.

11. The process of claim 10, wherein said step (a) is carried out at a temperature of 30° to 55° C.

* * * * *